United States Patent [19]

Cino et al.

[11] Patent Number: 5,527,702
[45] Date of Patent: Jun. 18, 1996

[54] CALLUS CELL INDUCTION FROM PARTIALLY SUBMERGED EXPLANT TISSUE IN LIQUID MEDIUM FOR PREPARATION OF TAXANES

[75] Inventors: Paul M. Cino, Bound Brook; Steven R. Schwarz, Milltown, both of N.J.; Dana L. Cazzulino, New York, N.Y.

[73] Assignee: E. R. Squibb & Sons, Inc., Princeton, N.J.

[21] Appl. No.: 202,718

[22] Filed: Feb. 23, 1994

Related U.S. Application Data

[63] Continuation of Ser. No. 864,826, Apr. 7, 1992, abandoned.
[51] Int. Cl.$^6$ .............................. C12N 5/00; C12P 17/04
[52] U.S. Cl. .................... 435/240.48; 435/126; 435/156; 435/240.54
[58] Field of Search .................................. 435/156, 174, 435/240.48, 240.54, 126

[56] References Cited

U.S. PATENT DOCUMENTS

| | | | |
|---|---|---|---|
| 2,747,334 | 5/1956 | Routien et al. | 47/58 |
| 3,955,317 | 5/1976 | Gudin | 435/240.46 |
| 4,038,778 | 8/1977 | Kadkade | 47/58 |
| 4,152,214 | 5/1979 | Delfel et al. | 195/104 |
| 4,352,887 | 10/1982 | Reid et al. | 435/240 |
| 4,463,522 | 8/1984 | Lindemann | 47/58 |
| 4,501,815 | 2/1985 | Reid et al. | 435/284 |
| 4,855,236 | 8/1989 | Levin | 435/240.45 |
| 4,910,138 | 3/1990 | Miura et al. | 435/119 |
| 4,960,703 | 10/1990 | Paques et al. | 435/240.45 |
| 5,019,504 | 5/1991 | Christen et al. | 435/240.48 |

FOREIGN PATENT DOCUMENTS

| | | |
|---|---|---|
| 2069122 | 11/1993 | Canada . |
| 052001 | 5/1982 | European Pat. Off. . |
| 291232 | 11/1988 | European Pat. Off. . |
| 553780 | 8/1993 | European Pat. Off. . |
| 577274 | 1/1994 | European Pat. Off. . |
| 5244971 | 9/1993 | Japan . |
| 86/04919 | 8/1986 | WIPO . |
| 92/13961 | 8/1992 | WIPO . |
| 93/00424 | 1/1993 | WIPO . |
| 93/02067 | 4/1993 | WIPO . |
| 93/10253 | 5/1993 | WIPO . |
| 93/17121 | 9/1993 | WIPO . |
| 93/21338 | 10/1993 | WIPO . |
| 93/19585 | 10/1993 | WIPO . |
| 93/23555 | 11/1993 | WIPO . |

OTHER PUBLICATIONS

Delfel et al., Antitumor Alkaloids in Callus Cultures . . . , 1977 pp. 1595–1598.
Misawa et al., Production of Antineoplastic Agents by Plant Tissue . . . , 1983, pp. 279–280.
Vidensek et al. Taxol Content . . . , 1990, pp. 1609–1610.
Yamada et al., Production of Useful Compounds in Culture, pp. 717–720.
Jaziri et al., "Enzyme–lined immunosorbent Assay for the Detection and the semi–quantitative Determination of Taxane Diterpenoids related to Taxol in Taxus sp. and Tissue Cultures", J. Pharm. Belg., 46, 2,93–99 (1991).
Eilert, Cell Culture and Somatic Cell Genetics of Plants, vol. 4, Academic Press, "Elicitation: Methodology and Aspects of Application", pp. 153–196 (1987).
Seibert et al., Light, Plant Tissue Culture as a Source of Biochemicals, Staba (ed), CRC Press, pp. 123–141 (1980).
Collinge, "Ways and means to plant secondary metabolites", Trends in Biotechnology, 4, pp. 299–301 (Dec. 1986).
Tabata, "Recent Advances in the Production of Medicinal Substances by Plant Cell Cultures", Plant Tissue Culture and Its Bio–technological Application, Proceedings of the First International Congress on Medicinal Plant Research, Section B, Sep. 6–10 (1976), Ed. W. Barz et al., pp. 3–16.
Erickson, "Secret Garden, Cell culture may provide a unique route to taxol", Scientific American, pp. 121–122 (Oct. 1991).
Wickremesinhe et al., "Habituated Callus Cultures of *Taxus media* cv. Hicksii as a source of Taxol", Annual Meeting of the American Society of Plant Physiologists, Plant Physiol., 96 (1 Supp.), (Jul.–Aug., 1991).
Wickremesinhe et al., Production of Taxol in callus and cell suspension cultures of *Taxus media* "Hicksii", In Vitro, Cellular & Developmental Biology, vol. 27, No. 3, Part II, 288 (mailed end of May, 1991) (presented at World Congress on Cell and Tissue Culture in Anaheim, CA between Jun. 16 and 20, 1991).
Kurz, "Semicontinuous Metabolite Production through Repeated Elicitation of Plant Cell Cultures: A Novel Process", Plant Biotechnology, Research Bottlenecks for Commercialization and Beyond (The University of Texas at Austin), pp. 1–7, 93–103, 202–203, Ed. Tom J. Mabry (1988).
Heinstein, "Future Approaches to the Formation of Secondary Natural Products in Plant Cell Suspension Cultures", J. Natural Products, vol. 48, No. 1, pp. 1–9 (Jan.–Feb. 1985).
"Plantlet Formation from Cultured Tissues and Cells", pp. 92–93 Plant Cell and Tissue Culture, Stafford and Warren (eds.); Open University Press (1991).

(List continued on next page.)

*Primary Examiner*—David M. Naff
*Assistant Examiner*—Deborah K. Ware
*Attorney, Agent, or Firm*—Suzanne E. Babajko

[57] ABSTRACT

A method for the induction of callus cells capable of producing taxanes from explant tissue by partially submerging the explant tissue in a liquid culture medium on a membrane raft, resulting in callus formation. The induction of callus cells by this method provides direct transfer of the cells formed to a liquid medium for a suspension cell culture preparation of taxanes. Thus, there is no need of a separate growth or proliferation step in the method of this invention. Furthermore, callus cells can be produced by the method; and also disclosed is a method for the use of the callus cells so produced in a suspension cell culture preparation for taxanes.

16 Claims, No Drawings

OTHER PUBLICATIONS

Morris et al., "Secondary Products Formation by Cell Suspension Cultures", Plant Cell Culture. A Practical Approach, Dixon (ed.), IRL Press, pp. 127–131 (1985).

Wickremesinhe et al., Detection of Taxol in Immature *Taxus media* and *Taxus cuspidata* stems, 88th Annual Meeting of the American Society for Horticultural Science, Jul. 19–24 (1991), Hortscience 26(6), 717 (1991).

Gibson et al., "Establishment of Cell Culture of *Taxus brevifolia* for Taxol and Ecdysone Production", Annual Meeting of the American Society of Plant Physiologists, Plant Physiol., 96 (1Supp.), (Jul.–Aug., 1991).

Christen et al., "Cell Culture as a Means to Produce Taxol", Eightieth Annual Meeting of the American Association for Cancer Research, Proc. Am. Cancer Res., May 24–27, 566 (1989).

Fett–Neto et al., "Cell Culture of Taxus as a Source of the Antineoplastic Drug Taxol and Related Taxanes", Biotechnology, vol. 10, 1572–1575 (Dec., 1992).

Bylinsky, "The Race for a Rare Cancer Drug", Fortune, pp. 100–102 (Jul., 1992).

Borman, "Scientists Mobilize to Increase Supply of Anticancer Drug Taxol", Chemical & Engineering News, pp. 11–18 (Sep. 1991).

Delfel et al., "Antitumor Alkaloids in Callus Cultures of *Cephalotaxus harringtonia*", Phytochemistry, 16:1595–1598 (1977).

Chemical Abstracts, 12060k, 74, p. 226 (1971).

Eilert et al., "Stimulation of Sanguinarine Accumulation in *Papaver somniferum* Cell Cultures by Fungal Elicitors", J. Plant Physiol., vol. 119, pp. 65–76 (1985).

Wani et al., "Plant Antitumor Agents. The Isolation and Structure of Taxol, a Novel Antileukemic and Antitumor Agent from *Taxus brevifolia*", J. Am. Chem. Soc., 93(9), 2325–2327 (1971).

Huang et al., "New Taxanes from *Taxus brevifolia*", J. Natural Products, vol. 49, No. 4, pp. 665–669 (Jul.–Aug. 1986).

DiCosmo et al., "Plant Cell Cultures and Microbial Insult: Interactions with Biotechnological Potential", Trends in Biotechnology 3(5):110–111 (1985).

Gamborg et al. in T. A. Thorpe, ed., Plant Tissue Culture, Academic Press, N.Y., p. 24 (1981).

Misawa et al., "Production of Antineoplastic Agents by Plant Tissue Cultures", Journal of Medicinal Plant Research, Planta Medica, vol. 49, pp. 115–119 (1983).

Chen et al., "Cryopreservation of wheat suspension culture and regenerable callus", Plants Cell Tissue Organ Culture, 4, pp. 101–109 (1985).

Rohr, "Production de cals par les gametophytes males de *Taxus baccata 1.* cultives sur en milieu artificiel. Etude en microsopie photonique et electronique", Caryologia, vol. 25, Supp, pp. 177–189 (1973).

Misawa et al., "Accumulation of Antineoplastic Agents by Plant Tissue Culture", Primary and Secondary Metabolism of Plant Cell Cultures, ed. by Neumann et al., Springer–Verlag Berlin Heidelberg, pp. 235–246 (1985).

Zenkteler et al., "Cytological Studies on the Regenerating Mature Female Gametophyte of *Taxus baccata* L. and Mature Endosperm of *Tilia platyphyllos* Scop. in in vitro Culture", Acta. Soc. Bot. Pol., 39(1); 161–173 (1970).

Westgate et al., "Growth of *Cephalotaxus harringtonia* plant–cell cultures", Appl. Microbiol. Biotechnol., 34:798–803 (1991).

Payne et al., "Plant Cell and Tissue Culture in Liquid Systems", Hanser Publishers, Munich, pp. 3 and 7 (1992).

Rowinsky et al., "Taxol: A Novel Investigational Antimicrotubule Agent", Journal of the National Cancer Institute, vol. 82, No. 15, pp. 1247–1259 (Aug. 1, 1990).

Flores et al., "In vitro culture and precocious germination of Taxus embryos", In Vitro Cell. Dev. Biol. Plant 27P(3), pp. 139–142 (1991) (abstract).

CALLUS CELL INDUCTION FROM PARTIALLY SUBMERGED EXPLANT TISSUE IN LIQUID MEDIUM FOR PREPARATION OF TAXANES

This is a continuation of application Ser. No. 07/864,826 filed on Apr. 7, 1992, now abandoned.

FIELD OF THE INVENTION

The present invention relates to a method for the induction of callus cells capable of producing taxanes such as taxol from explant tissues, to the callus cells so produced, and to a method employing these cells in the suspension cell culture preparation of taxanes.

BACKGROUND OF THE INVENTION

Taxanes are diterpene compounds which find utility in the pharmaceutical field. For example, taxol, a taxane having the structure:

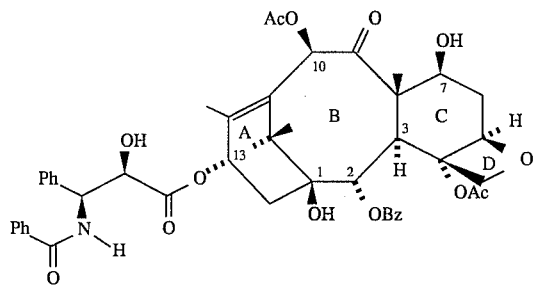

where Ph is phenyl, Ac is acetyl and Bz is benzoyl has been found to be an effective anticancer agent, particularly useful in the treatment of ovarian cancer.

Taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for alternate methods for obtaining taxanes such as taxol. Particularly sought are efficient methods for the suspension cell culture preparation of these compounds.

SUMMARY OF THE INVENTION

The present invention provides a method for the induction of callus cells capable of producing at least one taxane from explant tissue, comprising the steps of:

(a) contacting at least part of said explant tissue with a liquid medium without completely submerging said tissue in said medium; and (b) inducing callus cells to form.

Induction of callus cells according to the method of the present invention allows direct transfer of the cells so formed to a liquid medium for the suspension cell culture preparation of taxanes, without need of a separate growth or proliferation step, thus shortening the overall development time.

The present invention also provide callus cells produced by the above method of the present invention, and a method for the use of these cells in the suspension cell culture preparation of taxanes.

DETAILED DESCRIPTION OF THE INVENTION

The present invention is described in further detail as follows.

Definitions

The term "explant tissue", as used herein, denotes tissue from an original plant source, which tissue, for example, has not previously been contacted with an artificial liquid or solid medium for the formation of callus cells.

The term "induction", as used herein, denotes the initial dedifferentiation from the aforementioned explant tissue to form callus cells.

The term "callus cell", as used herein, denotes any cell which is dedifferentiated relative to the explant tissue from which it was derived.

The term "solid medium", as used herein, denotes a medium containing gelling agent(s) in a quantity sufficient for solidification of the medium.

The term "liquid medium", as used herein, denotes a medium containing gelling agent(s) in a quantity insufficient for solidification of that medium, or which contains no gelling agent(s) at all.

The term "dispersed cells", as used herein, denotes those callus cells or callus cell clusters which, upon dedifferentiation from explant tissue, do not adhere to the remaining explant tissue and thus become free cells or cell clusters in the surrounding liquid medium.

The term "membrane raft", as used herein, denotes a sheet-like support structure for the explant tissue, which structure is preferably sufficiently porous to allow transport of nutrients.

The term "dedifferentiation", as used herein, denotes changes in a differentiated tissue, which changes are of a kind leading to the reversion of cell type to a common cell type.

Explant tissue

The explant tissue employed in the method of the present invention may be any plant tissue from which callus cells capable of producing a taxane may be induced. Exemplary sources for explant tissue include plants of the family Taxaceae such as plants of the genera Amentotaxus, Austrotaxus, Pseudotaxus, Torreya, and Taxus. Preferred as sources of explant tissue are plants of the genus Taxus, particularly the species T. brevifolia, T. baccata, T. x media (e.g. Taxus media hicksii), T. wallichiana, T. canadensis, T. cuspidata, T. floridiana, T. celebica and T. x hunnewelliana.

Any part of the plant from which callus cells may be induced may be employed as the explant source such as the bark, cambium, roots, leaves or needles, stems, branches, twigs, wood, embryos, seeds or seedlings. Preferably, the plant organs comprising the root, stem, leaf or embryo are employed, particularly where the source of root tissue is from the root meristem (growing tip) or root cambrium (root bark), where the stem tissue is from bark, branches or twigs, and where the embryo tissue is from immature embryos or germinated mature embryos from seeds. The age or maturity of the plant employed as the explant source may range from that of immature embryos, embryos, seedlings, up to and including mature trees. Stem tissue is most preferred.

Preferably, prior to use in the present invention, the explant tissue is sectioned into pieces of a size suitable for use therein, such as sizes ranging from about 1 cm to about 5 cm in length. The surface of the explant tissue is also preferably sterilized before use. Sterilization may be conducted by any appropriate method such as by the use of chlorinated bleach, an alcohol solution such as an ethanol/water (e.g. 70% ethanol) solution, or a mixture thereof. Antimicrobial agents may also be employed to achieve and maintain sterility.

Support

The explant tissue employed in the present invention is maintained in a position such that at least part of the tissue is in contact with the liquid medium, while complete submersion in the liquid medium, which is undesirable for callus induction, is avoided. Thus, a support may employed which maintains the explant tissue in a position where a portion of the tissue is in contact with the surrounding atmosphere, most preferably air, while the remaining portion is in contact with the liquid medium.

Any support so positioning the explant tissue of the present invention may be employed. The explant tissue may, for example, be placed on a membrane raft, which is preferred, or on a sponge. Preferred materials for use as a membrane raft include microporous polypropylene or cellulose acetate. It is preferred that the average diameter of the pores of the raft is smaller than the average diameter of the individual callus cells which are formed. Particularly preferred are those membrane materials which do not allow the transfer of callus cells across the membrane. It is also preferred that the level of the liquid medium be above the level of the membrane raft, such as where the raft is positioned below the level of the liquid medium so that there is liquid both above and below the level of the raft. These embodiments facilitate the formation of dispersed cells, and, especially, clusters of dispersed cells.

Liquid Medium

Any liquid medium allowing callus induction may be employed. Exemplary liquid media are aqueous media of Gamborg's B5 (Table 1 following), Murashige and Skoog (Table 2 following), Anderson's Rhododendron Basal Salts (Table 3 following), Whites (Table 4 following), as well as variations of these media. Exemplary variations of the aforementioned media include the addition of sugars such as sucrose, glucose or maltose, casamino acids (e.g. 0.2%), enzyme hydrolyzed casein (e.g. 0.02%), and glycine (e.g. 0.002%) and various auxins and cytokinins. The use of aqueous Gamborg's B5 medium is preferred.

TABLE 1

Composition of Gamborg's B5 Medium

| | mg/L |
|---|---|
| Basal Salts | |
| Ammonium sulfate | 134.000 |
| Boric acid | 3.000 |
| Calcium chloride anhydrous | 113.240 |
| Cobalt chloride hexahydrate | 0.025 |
| Cupric sulfate pentahydrate | 0.025 |
| Disodium EDTA dihydrate | 37.300 |
| Ferrous sulfate heptahydrate | 27.800 |
| Magnesium sulfate anhydrous | 122.090 |
| Manganese sulfate monohydrate | 10.000 |
| Potassium iodide | 0.750 |
| Potassium nitrate | 2500.000 |
| Sodium molybdate dihydrate | 0.250 |
| Sodium phosphate monobasic anhydrous | 130.500 |
| Zinc sulfate heptahydrate | 2.000 |
| Vitamins | |
| Myo-inositol | 100.0 |
| Thiamine HCl | 10.0 |

TABLE 1-continued

Composition of Gamborg's B5 Medium

| | mg/L |
|---|---|
| Pyridoxine HCl | 1.0 |
| Nicotinic acid | 1.0 |
| Sugars | |
| Sucrose | 20,000.0 |
| Hormones | |
| 2,4-Dichlorophenoxyacetic acid ("2,4-D") | 1.5 |

TABLE 2

Composition of Murashige and Skoog Medium

| | mg/L |
|---|---|
| Basal Salts | |
| Boric acid | 6.20 |
| Calcium chloride anhydrous | 332.20 |
| Cobalt chloride hexahydrate | 0.025 |
| Cupric sulfate pentahydrate | 0.025 |
| Disodium EDTA dihydrate | 37.260 |
| Ferrous sulfate heptahydrate | 27.800 |
| Magnesium sulfate anhydrous | 180.70 |
| Manganese sulfate monohydrate | 16.90 |
| Potassium iodide | 0.830 |
| Potassium nitrate | 1900.00 |
| Sodium molybdate dihydrate | 0.250 |
| Potassium phosphate monobasic anhydrous | 170.00 |
| Zinc sulfate heptahydrate | 8.60 |
| Ammonium Nitrate | 1650.00 |
| Vitamins | |
| Myo-inositol | 100.0 |
| Thiamine HCl | 10.0 |
| Pyridoxine HCl | 1.0 |
| Nicotinic acid | 1.0 |
| Sugars | |
| Sucrose | 20,000.0 |
| Hormones | |
| 2,4-Dichlorophenoxyacetic acid | 1.5 |

TABLE 3

Composition of Anderson's Rhododendron Basal Salts Medium

| | mg/L |
|---|---|
| Basal Salts | |
| Ammonium nitrate | 400.00 |
| Boric acid | 6.200 |
| Calcium chloride anhydrous | 332.20 |
| Cobalt chloride hexahydrate | 0.025 |
| Cupric sulfate pentahydrate | 0.025 |
| Disodium EDTA dihydrate | 74.500 |
| Ferrous sulfate heptahydrate | 55.70 |
| Magnesium sulfate anhydrous | 180.70 |
| Manganese sulfate monohydrate | 16.90 |
| Potassium iodide | 0.300 |
| Potassium nitrate | 480.00 |
| Sodium molybdate dihydrate | 0.250 |
| Sodium phosphate monobasic anhydrous | 330.60 |
| Zinc sulfate heptahydrate | 8.60 |
| Vitamins | |
| Myo-inositol | 100.0 |
| Thiamine HCl | 10.0 |
| Pyridoxine HCl | 1.0 |

TABLE 3-continued

Composition of Anderson's Rhododendron Basal Salts Medium

| | mg/L |
|---|---|
| Nicotinic acid | 1.0 |
| Sugars | |
| Sucrose | 20,000.0 |
| Hormones | |
| 2,4-Dichlorophenoxyacetic acid | 1.5 |

TABLE 4

Composition of Whites Medium

| | mg/L |
|---|---|
| Basal Salts | |
| Boric acid | 1.50 |
| Calcium nitrate tetrahydrate | 208.40 |
| Cupric sulfate pentahydrate | 0.010 |
| Ferric sulfate | 2.50 |
| Magnesium sulfate anhydrous | 366.20 |
| Manganese sulfate monohydrate | 3.788 |
| Potassium iodide | 0.750 |
| Potassium nitrate | 80.00 |
| Sodium sulfate | 200.00 |
| Sodium phosphate monobasic anhydrous | 16.50 |
| Zinc sulfate heptahydrate | 3.00 |
| Potassium chloride | 65.00 |
| Vitamins | |
| Myo-inositol | 100.0 |
| Thiamine HCl | 10.0 |
| Pyridoxine HCl | 1.0 |
| Nicotinic acid | 1.0 |
| Sugars | |
| Sucrose | 20,000.0 |
| Hormones | |
| 2,4-Dichlorophenoxyacetic acid | 1.5 |

Callus Induction

Callus cells may be induced by holding the explant tissue/liquid medium system at suitable conditions therefor.

The temperature employed during induction is preferably between about 20° C. and about 30° C., most preferably about 22° C. The portion of the explant tissue not in contact with the liquid medium is preferably in contact with air in which the relative humidity is controlled, for example, by tightly sealing the system. The relative humidity may, for example, be near saturation such as between about 80% and about 100%. Diffuse, that is, ordinary room lighting, is preferred.

The portion of the explant tissue which is in contact with the liquid medium is preferably from about 10% to about 25% of the total volume of the tissue section. Induction is preferably conducted over a period between about 10 days to about 30 days. Gentle agitation of the liquid medium in contact with the explant tissue during induction may be employed, although quiescent conditions are preferred.

Callus cells may form which remain adhered to the remaining explant tissue and/or which slough off the remaining explant tissue to form free callus cells or cell clusters dispersed in the surrounding liquid medium ("dispersed cells"). Some initial proliferation of the callus cells formed may occur during the present induction method.

Use of a liquid, rather than solid, medium in the induction of callus cells according to the method of the present invention provides significant advantages. Specifically, use of a solid medium induces callus formation in a relatively dry environment in which the callus cells formed remain adhered to the explant tissue. Callus cells formed in such an environment, in order to ultimately grow and produce taxanes efficiently in liquid suspension cell culture, must be acclimated to a liquid environment. Due to the change in oxygen availability, osmotic differences and the like, callus cells induced on a solid medium, during acclimation to a liquid environment, undergo a decrease in growth rate and taxane production, and may exhibit an increase in cell-type abnormalities and lysis. Moreover, acclimation, particularly when achieved during a separate, subsequent growth or proliferation step, lengthens the overall development time from explant tissue to liquid suspension cell culture.

The method of the present invention obviates the above difficulties. Callus cells induced in contact with a liquid medium, particularly dispersed callus cells so induced as described above, are more readily acclimated to liquid suspension cell culture conditions. Callus cells induced by the method of the present invention may be transferred directly to a liquid suspension cell culture medium without employing a separate growth or proliferation step. Thus, the induction method of the present invention is efficient in reducing the overall development time from explant tissue to suspension cell culture, improving productivity.

Other advantages may also be obtained by the method of the present invention. For example, callus induction may be achieved for a longer time period on a liquid, rather than solid, medium so that a greater number of callus cells may be obtained. Undesirable compounds, such as phenolics, produced during callus induction are more readily diffused into the medium and away from the callus induction site when employing a liquid medium. Further, the callus formed by the method of the present invention has a healthy, green appearance and contains fewer brown callus cell areas than callus induced on a solid medium.

The preferred embodiments of the present invention provide additional advantages. For example, the formation of dispersed cells and dispersed cell clusters is desirable as such cells are most readily acclimated to liquid suspension cell culture conditions. Thus, use of a liquid medium in contact with a sufficient portion of the explant tissue so as to allow and promote the formation of dispersed cells and cell clusters, such as where the level of the liquid medium is above that of the explant tissue supporting structure (e.g. membrane raft), is advantageous.

Most advantageous is the formation of clusters of dispersed cells. Clusters of dispersed cells, when transferred to a liquid suspension cell culture system, most rapidly achieve the critical mass of cells required for maximum cell growth and taxane output. Thus, use of an explant tissue supporting structure which does not allow the transfer of dispersed cell clusters across the structure is preferred. For example, use of a membrane raft which has pores the average diameter of which is smaller than the average diameter of individual dispersed cells, retains cell clusters above the level of the raft and inhibits the transfer of cells across the membrane during which cell clusters may be broken up into individual cells.

Taxane Production

The present invention also provides a method for the production of at least one taxane, comprising the steps of:

(A) inducing callus cells capable of producing at least one taxane according the above-described method of the present invention for callus cell induction; and (B) culturing said cells in a liquid suspension cell culture system to produce said taxane(s).

It is preferred to proceed from step (A) to step (B) without use of an intermediate, separate growth or proliferation step. By "separate growth or proliferation step", as used herein, is meant transferring the cells to a site physically distinct from that where steps (A) and (B) are conducted, and growing or proliferating callus cells.

The suspension cell culture of any taxane capable of being produced by such a method is contemplated within the scope of the present invention. It is understood herein that a single, or two or more taxanes, may be produced during practice of the method of the present invention.

The culturing step (B) of the above method of the present invention may be carried out according to suspension cell culture methods such as those known to the skilled artisan. See U.S. Pat. No. 5,019,504, incorporated by reference. Exemplary media which may be employed include those discussed above with respect to induction media. Agar (e.g. 0.1%) or phytagel (e.g. 0.025%) may optionally further be added to such media. The temperature employed during suspension cell culture is preferably between about 22° and 25° C.; the relative humidity employed is preferably between about 40 and about 60%; and the degree of agitation is preferably from about 30 to about 200 revolutions per minute (RPM). Inducers such as fungal elicitors, vanadyl sulfate, 3,4-dichlorophenoxy triethyl(amine), etc. may be added. Taxane production may also be conducted by employing cells which are encapsulated in calcium alginate beads, as well as when in a slurry, e.g. made by incorporation of 0.1% agar into the media.

Recovery of the taxanes produced during culturing may be accomplished by methods known to the skilled artisan. For example, adsorbent beads may be employed to expedite recovery of taxanes such as taxol. Beads remaining in the culture during the production of taxanes such as taxol may also allow greater production by binding the taxane product(s). Additionally, extraction of the taxane product(s) from the cell supernatant or beads is readily accomplished with solvents such as ether or methylene chloride.

Taxane Compounds

Taxanes are diterpene compounds containing the taxane carbon skeleton:

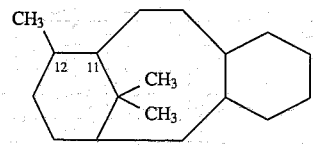

which skeleton may contain ethylenic unsaturation in the ring system thereof (e.g., where the 11,12-positions are bonded through an ethylenic linkage). The preparation of all taxanes, whether pharmacologically active or inactive, is contemplated within the scope of the present invention. Taxanes may be produced by the callus cells of the present invention which are (i.e. are naturally occuring), or are not, found in the original explant tissue.

Exemplary taxanes which may be produced by the cell culture method of the present invention include those of the following formula I:

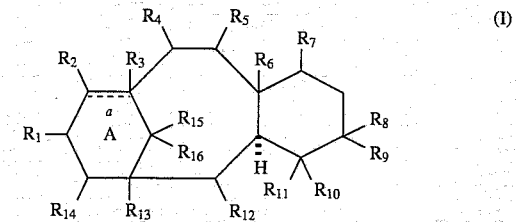

where $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$ and "a" are as defined in the following Table 5.

TABLE 5

| Compound[4/] | $R_1$[1/] | $R_2$ | $R_3$ | $R_4$ | $R_5$ | $R_6$ | $R_7$[2/] | $R^8$ |
|---|---|---|---|---|---|---|---|---|
| 1) taxol | tax | $CH_3$ | H | β-acetyloxy | =O | β-$CH_3$ | β-OH | H |
| 2) 10-desacetyl-cephalomannine | ceph | $CH_3$ | H | β-OH | =O | β-$CH_3$ | β-OH | H |
| 3) 7-epitaxol | tax | $CH_3$ | H | β-acetyloxy | =O | β-$CH_3$ | α-OH | H |
| 4) 10-desacetyl-7-epitaxol | tax | $CH_3$ | H | β-OH | =O | β-$CH_3$ | α-OH | H |
| 5) 7-epicephalo-mannine | ceph | $CH_3$ | H | β-acetyloxy | =O | β-$CH_3$ | α-OH | H |
| 6) baccatin III | α-OH | $CH_3$ | H | β-acetyloxy | =O | β-$CH_3$ | β-OH | H |
| 7) 10-desacetyl-baccatin III | α-OH | $CH_3$ | H | β-OH | =O | β-$CH_3$ | β-OH | H |
| 8) cephalomannine | ceph | $CH_3$ | H | β-acetyloxy | =O | β-$CH_3$ | β-OH | H |
| 9) 10-desacetyl-taxol | tax | $CH_3$ | H | β-OH | =O | β-$CH_3$ | β-OH | H |
| 10) xylosyl taxol | tax | $CH_3$ | H | β-acetyloxy | =O | β-$CH_3$ | β-xylosyl | H |
| 11) xylosyl ceph-alomannine | ceph | $CH_3$ | H | β-acetyloxy | =O | β-$CH_3$ | β-xylosyl | H |
| 12) taxagifine | =O | α-$CH_3$ | β-OH | β-acetyloxy | α-acetyloxy | β-$CH_3$ | β-acetyloxy | H |
| 13) 8-benzoyloxy taxagifine | =O | α-$CH_3$ | β-OH | β-acetyloxy | α-acetyloxy | β-benzoyl-oxymethyl | β-acetyloxy | H |
| 14) 9-acetyloxy-taxusin | α-acetyloxy | $CH_3$ | H | β-acetyloxy | α-acetyloxy | β-$CH_3$ | H | H |
| 15) 9-hydroxytaxusin | α-acetyloxy | $CH_3$ | H | β-acetyloxy | α-OH | β-$CH_3$ | H | H |
| 16) taiwanxan | H | $CH_3$ | H | β-acetyloxy | α-acetyloxy | β-$CH_3$ | H | H |
| 17) taxane Ia | tax | $CH_3$ | H | =O | =O | β-$CH_3$ | α-OH | H |
| 18) taxane Ib | taxsub | $CH_3$ | H | =O | =O | β-$CH_3$ | α-OH | H |
| 19) taxane Ic | taxsub | $CH_3$ | H | =O | =O | β-$CH_3$ | α-acetyloxy | H |
| 20) taxane Id | α-acetyloxy | $CH_3$ | H | β-acetyloxy | α-acetyloxy | β-$CH_3$ | β-acetyloxy | H |
| 21) 7-epibaccatin III | α-OH | $CH_3$ | H | β-acetyloxy | =O | β-$CH_3$ | α-OH | H |
| 22) taxotere | taxot | $CH_3$ | H | β-OH | =O | β-$CH_3$ | β-OH | H |

TABLE 5-continued

| Compound[4/] | $R_9$[5/] | $R_{10}$ | $R_{11}$ | $R_{12}$ | $R_{13}$ | $R_{14}$ | $R_{15}$ | $R_{16}$ | a[3/] |
|---|---|---|---|---|---|---|---|---|---|
| 1) taxol | | oxetane | α-acetyloxy | α-benzoyloxy | β-OH | H | $CH_3$ | $CH_3$ | X |
| 2) 10-desacetyl-cephalomannine | | oxetane | α-acetyloxy | α-benzoyloxy | β-OH | H | $CH_3$ | $CH_3$ | X |
| 3) 7-epitaxol | | oxetane | α-acetyloxy | α-benzoyloxy | β-OH | H | $CH_3$ | $CH_3$ | X |
| 4) 10-desacetyl-7-epitaxol | | oxetane | α-acetyloxy | α-benzoyloxy | β-OH | H | $CH_3$ | $CH_3$ | X |
| 5) 7-epicephalomannine | | oxetane | α-acetyloxy | α-benzoyloxy | β-OH | H | $CH_3$ | $CH_3$ | X |
| 6) baccatin III | | oxetane | α-acetyloxy | α-benzoyloxy | β-OH | H | $CH_3$ | $CH_3$ | X |
| 7) 10-desacetyl-baccatin III | | oxetane | α-acetyloxy | α-benzoyloxy | β-OH | H | $CH_3$ | $CH_3$ | X |
| 8) cephalomannine | | oxetane | α-acetyloxy | α-benzoyloxy | β-OH | H | $CH_3$ | $CH_3$ | X |
| 9) 10-desacetyl-taxol | | oxetane | α-acetyloxy | α-benzoyloxy | β-OH | H | $CH_3$ | $CH_3$ | X |
| 10) xylosyl taxol | | oxetane | α-acetyloxy | α-benzoyloxy | β-OH | H | $CH_3$ | $CH_3$ | X |
| 11) xylosyl cephalomannine | | oxetane | α-acetyloxy | α-benzoyloxy | β-OH | H | $CH_3$ | $CH_3$ | X |
| 12) taxagifine | α-cinnamoyloxy | | methylene (=$CH_2$) | α-acetyloxy | β-H | H | cyclo[6/] | α-$CH_3$ | — |
| 13) 8-benzoyloxy taxagifine | α-cinnamoyloxy | | methylene (=$CH_2$) | α-acetyloxy | β-H | H | cyclo | α-$CH_3$ | — |
| 14) 9-acetyloxy taxusin | α-acetyloxy | | methylene (=$CH_2$) | H | H | H | $CH_3$ | $CH_3$ | X |
| 15) 9-hydroxy taxusin | α-acetyloxy | | methylene (=$CH_2$) | H | H | H | $CH_3$ | $CH_3$ | X |
| 16) taiwanxan | α-OH | | methylene (=$CH_2$) | α-acetyloxy | H | 2-methylbutanoyloxy | $CH_3$ | $CH_3$ | X |
| 17) taxane Ia | | oxetane | α-acetyloxy | α-benzoyloxy | β-OH | H | $CH_3$ | $CH_3$ | X |
| 18) taxane Ib | | oxetane | α-acetyloxy | α-benzoyloxy | β-OH | H | $CH_3$ | $CH_3$ | X |
| 19) taxane Ic | | oxetane | α-acetyloxy | α-benzoyloxy | β-OH | H | $CH_3$ | $CH_3$ | X |
| 20) taxane Id | α-OH | | epoxide[7/] | α-acetyloxy | β-OH | H | $CH_3$ | $CH_3$ | X |
| 21) 7-epibaccatin III | | oxetane | α-acetyloxy | α-benzoyloxy | β-OH | H | $CH_3$ | $CH_3$ | X |
| 22) taxotere | | oxetane | α-acetyloxy | α-benzoyloxy | β-OH | H | $CH_3$ | $CH_3$ | X |

Footnotes

[1/]"ceph" denotes

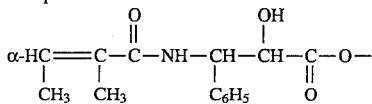

"tax" denotes

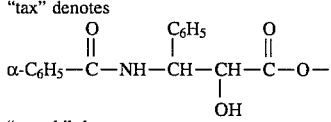

"taxsub" denotes

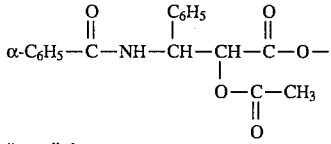

"taxot" denotes

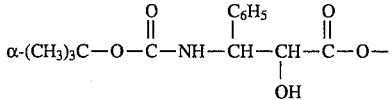

[2/]"xylosyl" denotes 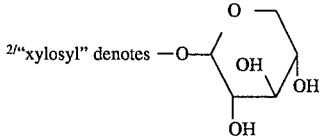

[3/]"a" denotes a double bond present between the 11- and 12-positions

[4/]"α" denotes the stereoposition of a moiety below the plane of the taxane ring structure shown above shown above (" 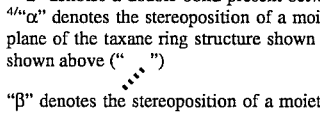 ")

"β" denotes the stereoposition of a moiety above the plane of the taxane ring structure shown above shown above (" ")

5/"oxetane" denotes the moiety 

which is 

6/"cyclo" denotes the cyclic group formed by bonding the group "O—" to the taxene A ring as follows:

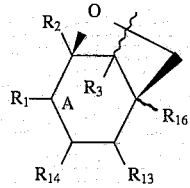

7/"epoxide" denotes the moiety 

Taxanes which may be produced by the cell culture method of the present invention may also be represented by the following formulae II or III:

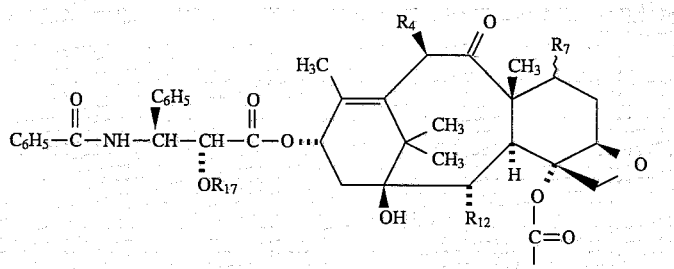

(II)

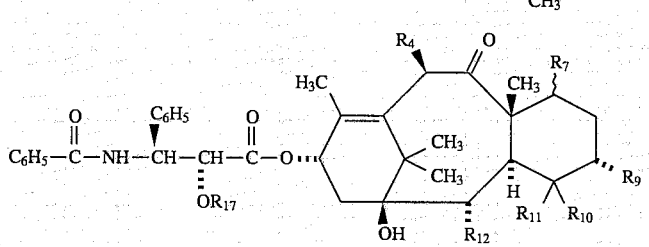

(III)

where $R_4$ is keto (=O) or acetyloxy;

$R_7$ is hydrogen, α-hydroxy or β-hydroxy;

$R_9$ is acetyloxy, cinnamoyloxy or hydroxyl;

$R_{10}$ and $R_{11}$ together form a methylene or epoxide group;

$R_{12}$ is hydrogen, benzoyloxy or acetyloxy; and $R_{17}$ is hydrogen or acetyloxy.

Preferred taxanes include taxol, baccatin III, 10-desacetylbaccatin III, 10-desacetyl taxol, xylosyl taxol, 7-epitaxol, 7-epibaccatin III and 10-desacetyl-7-epitaxol. Cell culture production of taxol is a particularly preferred embodiment of the present invention.

Taxanes are compounds which find utility in the pharmaceutical field, such as in the treatment of cancer. Taxol is exemplary of the pharmacologically active taxanes which also include, for example, cephalomannine, the latter reported as a chemotherapeutic agent for the remission of leukemia in U.S. Pat. No. 4,206,221. The present invention contemplates preparation of such pharmacologically active taxanes, as well as preparation of slightly active or inactive taxanes, or those having a less desired activity, which may be used as intermediates to prepare other, pharmacologically active taxanes. The method of the present invention may thus facilitate preparation of pharmacologically active taxanes by providing an efficient means for obtaining the taxane starting material through cell culture.

The methods of the present invention are further described by the following Examples. These Examples are illustrative only, and are in no way intended to limit the scope of the instant claims.

EXAMPLE 1

Induction of Callus Cells and Preparation of Taxol

Explants were cut from *Taxus media hicksii* plant stems after sterilizing in 70% alcohol and 25% bleach. Each explant, approximately 2–3 cm in length, was placed on a microporous polypropylene membrane raft which was floating on a medium consisting of Gamborg's B5 Basal salts and vitamins (see previous Table 1), sucrose (2%), 2,4-D (1.5 mg/L) and casamino acids (2 g/L). The medium and raft were contained in a 4×4 inch polycarbonate container fitted with a tight polypropylene lid so as to maintain high humidity.

Prior to placing the explant on the raft, the vessel and medium were autoclaved under standard conditions for 15 minutes. After placing the explant on the raft, 5–10 ml of the above medium were placed on top of the explant. The raft vessel was incubated at 22° C. for 3–4 weeks until a callus had been generated. After incubation, the explant and callus were removed and the loose cells remaining on the raft were pipetted off and added to 25 ml of the above Gamborg's medium to which had been added 0.1 g/L agar in a 125 ml flask. The loose cells from several rafts may be combined into one flask if cell numbers appear to be low. The inoculated flask was incubated at 22° C. on a 50 RPM shaker with 45% humidity and diffuse light.

After 3 weeks, flasks were harvested and analyzed for taxol. Suspension flasks were found to contain 0.01 to 0.02 mg/L taxol or expressed on a dry cell weight basis: 0.0002 to 0.0004% taxol based on dry cell weight. The presence of other taxanes including cephalomannine and baccatin III was also detected. (Based on two runs as follows:

| Run | Taxol Obtained (μg/ml) | Dry Cell weight (mg/ml) |
|---|---|---|
| 1 | 0.0207 | 5.5 |
| 2 | 0.0131 | 5.7) |

EXAMPLE 2

Variation In Medium

Explants were cut from *Taxus media hicksii* plant stems after sterilizing in 70% alcohol and 25% bleach. Each explant, approximately 2–3 cm in length, was placed on a microporous polypropylene membrane raft which was floating on a medium consisting of Anderson's Rhododendron basal salts (see previous Table 3) and Gamborg's vitamins (see previous Table 1), sucrose (2%), 2,4-D (1.5 mg/L) and casamino acids (2 g/L). The medium and raft were contained in a 4×4 inch polycarbonate container fitted with a tight polypropylene lid so as to maintain high humidity.

Prior to placing the explant on the raft, the vessel and medium were autoclaved under standard conditions for 15 minutes. After placing the explant on the raft, 5–10 ml of the above medium were placed on top of the explant. The raft vessel was incubated at 22° C. for 5–10 weeks until a callus had been generated. After incubation, the explant and callus were removed and the loose cells remaining on the raft were pipetted off and added to 25 ml of the above Anderson's medium to which had been added 0.1 g/L agar in a 125 ml flask. (Loose cells from several rafts may be combined as described above in Example 1.) The inoculated flask was incubated at 22° C. on a 50 RPM shaker with 45% humidity and diffuse light.

After 3 weeks, flasks were harvested and analyzed for taxol. Suspension flasks were found to contain 0.0194 mg/L taxol or expressed on a dry cell weight basis: 0.0062% taxol based on dry cell weight.

What we claim is:

1. A method for the induction of callus cells capable of producing at least one taxane, wherein said callus cells are formed from explant tissue, comprising the steps of:
    (a) contacting said explant tissue with a liquid medium without completely submerging said tissue in said medium; and
    (b) holding the explant tissue and liquid medium at conditions suitable for the induction of callus cells, whereby callus cells are formed which are capable of producing at least one taxane.

2. The method of claim 1, wherein said explant tissue is obtained from a plant of the family Taxaceae.

3. The method of claim 2, wherein said plant is selected from the group consisting of the species *T. brevifolia, T. baccata, T. x media, T. wallichiana, T. canadensis, T. cuspidata, T. floridiana, T. celebica* and *T. x hunnewelliana*.

4. The method of claim 1, wherein said at least one taxane is taxol, 10-desacetylcephalomannine, 7-epitaxol, 10-desacetyl-7-epitaxol, 7-epicephalomannine, baccatin III, taxotere, 10-desacetylbaccatin III, cephalomannine, 10-desacetyltaxol, xylosyl taxol, xylosyl cephalomannine, 7-epibaccatin III, taxagifine, 8-benzoyloxy taxagifine, 9-acetyloxy taxusin, 9-hydroxy taxusin, taiwanxam, taxane Ia, taxane Ib, taxane Ic and/or taxane Id.

5. The method of claim 4, wherein said at least one taxane is taxol, baccatin III, 10-desacetylbaccatin III, 10-desacetyltaxol, xylosyl taxol, 7-epibaccatin III, 7-epitaxol and/or 10-desacetyl-7-epitaxol.

6. The method of claim 5, wherein said taxane is taxol.

7. The method of claim 1, wherein said at least one taxane is a taxane of the formula II and/or III:

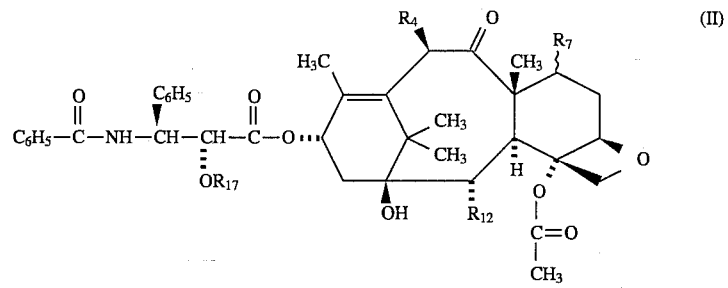

-continued

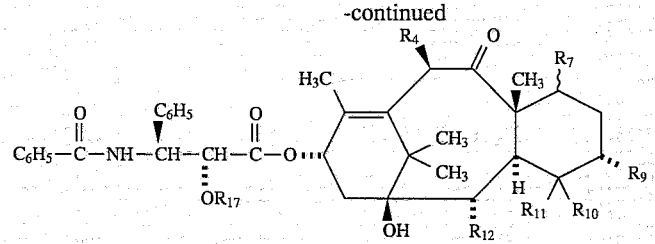
(III)

where
- $R_4$ is keto (=O) or acetyloxy;
- $R_7$ is hydrogen, α-hydroxy or β-hydroxy;
- $R_9$ is acetyloxy, cinnamoyloxy or hydroxyl;
- $R_{10}$ and $R_{11}$ together form a methylene or epoxide group;
- $R_{12}$ is hydrogen, benzoyloxy or acetyloxy; and
- $R_{17}$ is hydrogen or acetyloxy.

8. The method of claim 1, wherein said explant tissue is supported on a membrane raft.

9. The method of claim 8, wherein said membrane raft is microporous polypropylene or cellulose acetate.

10. The method of claim 8, wherein the level of said liquid medium is above the level of said raft.

11. The method of claim 10, wherein dispersed callus cells are formed, wherein said cells are free cells or cell clusters, and, further, wherein at least some of said dispersed cells remain above the level of said raft.

12. The method of claim 11, wherein said raft is a porous structure in which the average diameter of the pores is smaller than the average diameter of the individual dispersed cells.

13. The method of claim 1, wherein said liquid medium is aqueous Gamborg's B5 medium, Murashige and Skoog medium, Anderson's Rhododendron Basal Salts medium or Whites medium.

14. The method of claim 13, wherein said liquid medium is aqueous Gamborg's B5 medium.

15. The method of claim 1, wherein the part of said explant tissue which is in contact with said liquid medium is from about 10% to about 25% of the total volume of said tissue.

16. The method of claim 1, wherein said explant tissue has not previously been contacted with an artificial liquid or solid medium for the formation of callus cells.

* * * * *